United States Patent
Dasgupta

(10) Patent No.: US 9,677,999 B2
(45) Date of Patent: Jun. 13, 2017

(54) CAVITY ENHANCEMENT METHODS, SYSTEMS AND DEVICES, AND METHODS OF MEASURING SAME

(71) Applicant: Purnendu K Dasgupta, Arlington, TX (US)

(72) Inventor: Purnendu K Dasgupta, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 130 days.

(21) Appl. No.: 14/670,269

(22) Filed: Mar. 26, 2015

(65) Prior Publication Data

US 2015/0308942 A1    Oct. 29, 2015

Related U.S. Application Data

(60) Provisional application No. 61/970,387, filed on Mar. 26, 2014.

(51) Int. Cl.
| | | |
|---|---|---|
| *G01N 21/00* | (2006.01) | |
| *G01N 21/31* | (2006.01) | |
| *G01N 21/03* | (2006.01) | |

(52) U.S. Cl.
CPC ........... *G01N 21/31* (2013.01); *G01N 21/031* (2013.01)

(58) Field of Classification Search
CPC .... G01N 21/03; G01N 21/031; G01N 21/534; G01N 21/39; G01J 3/2803; G01J 3/42
USPC ......................... 356/436–437, 402, 440, 326
See application file for complete search history.

(56) References Cited

U.S. PATENT DOCUMENTS

| | | | |
|---|---|---|---|
| 6,020,207 A * | 2/2000 | Liu | G01N 21/0303 |
| | | | 422/82.08 |
| 6,542,231 B1 * | 4/2003 | Garrett | G01N 21/05 |
| | | | 250/227.11 |
| 6,839,140 B1 | 1/2005 | O'Keefe | |
| 6,940,600 B1 * | 9/2005 | Smith | G01N 21/031 |
| | | | 356/437 |
| 7,236,248 B2 * | 6/2007 | Kirkpatrick | G01J 3/433 |
| | | | 356/435 |
| 7,468,797 B1 * | 12/2008 | O'Keefe | G01J 3/42 |
| | | | 356/437 |

(Continued)

OTHER PUBLICATIONS

Lanridge et al., "Cavity enhanced absorption spectroscopy of multiple trace gas species using a supercontinuum radiation source", Jul. 7, 2008 / vol. 16, No. 14 / Optics Express 10178.

(Continued)

*Primary Examiner* — Tarifur Chowdhury
*Assistant Examiner* — Isiaka Akanbi
(74) *Attorney, Agent, or Firm* — FisherBroyles, LLP; Anthony J. DoVale

(57) ABSTRACT

A system for increasing light throughput in cavity enhanced spectrometry, and a model for cavity enhanced absorption measurements are presented. The cavity has an entrance mirror, an opposed exit mirror and a detector positioned adjacent the exit mirror. An input aperture is defined in the entrance mirror to allow light from a source to enter the cavity. The input aperture improves light throughput without significant departure from the theoretically predicted amplification of absorbance. This results in improvement of detection limits, even with mirrors of modest reflectivity and inexpensive detectors.

18 Claims, 8 Drawing Sheets

(56) References Cited

U.S. PATENT DOCUMENTS

| | | | | |
|---|---|---|---|---|
| 8,098,377 B2* | 1/2012 | Gundersen | ........... | G01N 21/532 250/339.07 |
| 2010/0002234 A1* | 1/2010 | Cormier | ................ | G01N 21/39 356/436 |
| 2013/0027705 A1* | 1/2013 | Berman | ............... | G01N 21/031 356/402 |

OTHER PUBLICATIONS

Li et al., "Nonlinear Absorbance Amplification Using a Diffuse Reflectance Cell: Total Organic Carbon Monitoring at 214 nm", Dec. 16, 2014, Anal. Chem. 2015, 87, 1111-1117.

Dasgupta et al., "Cavity-Enhanced Absorption Measurements Across Broad Absorbance and Reflectivity Ranges", Mar. 19, 2014, Anal. Chem. 2014, 86, 3727-3734.

* cited by examiner

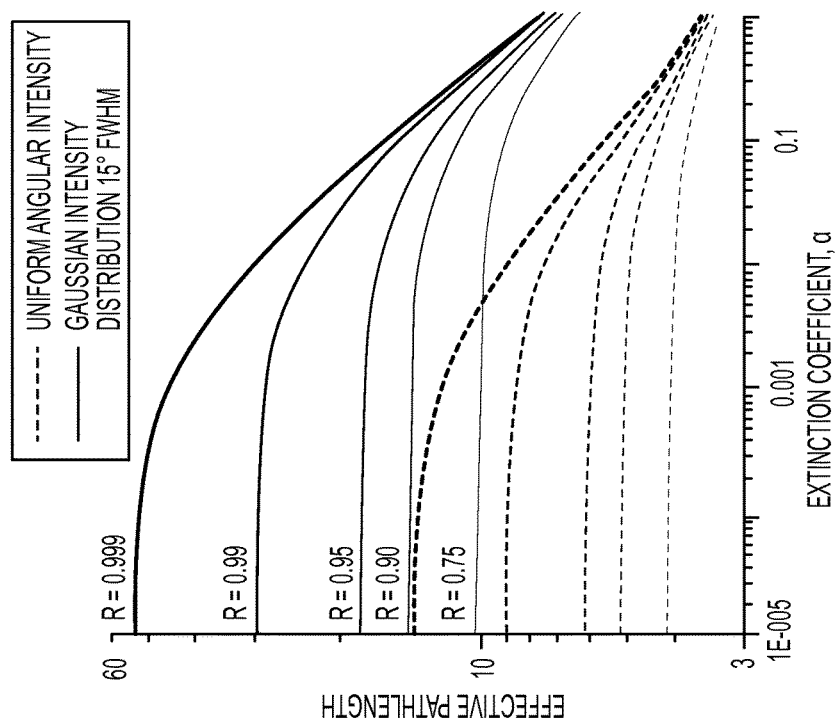
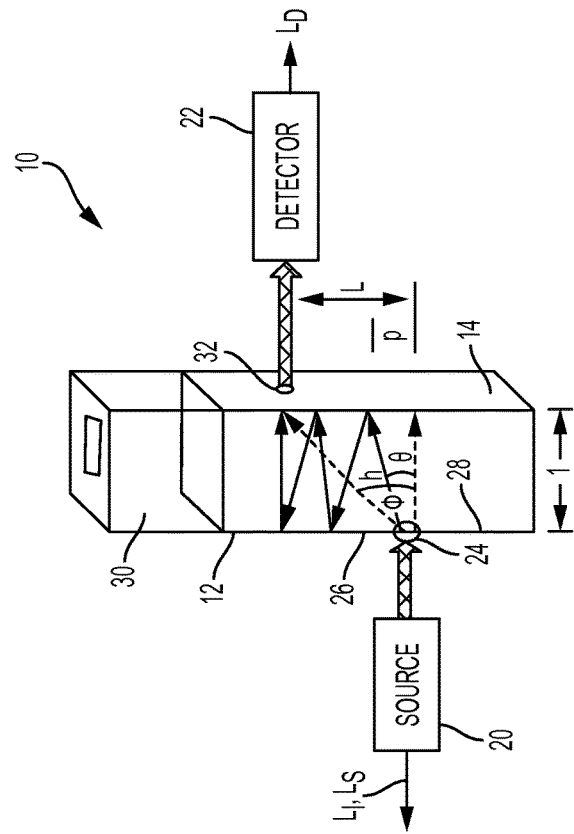
FIG. 3A
FIG. 3B

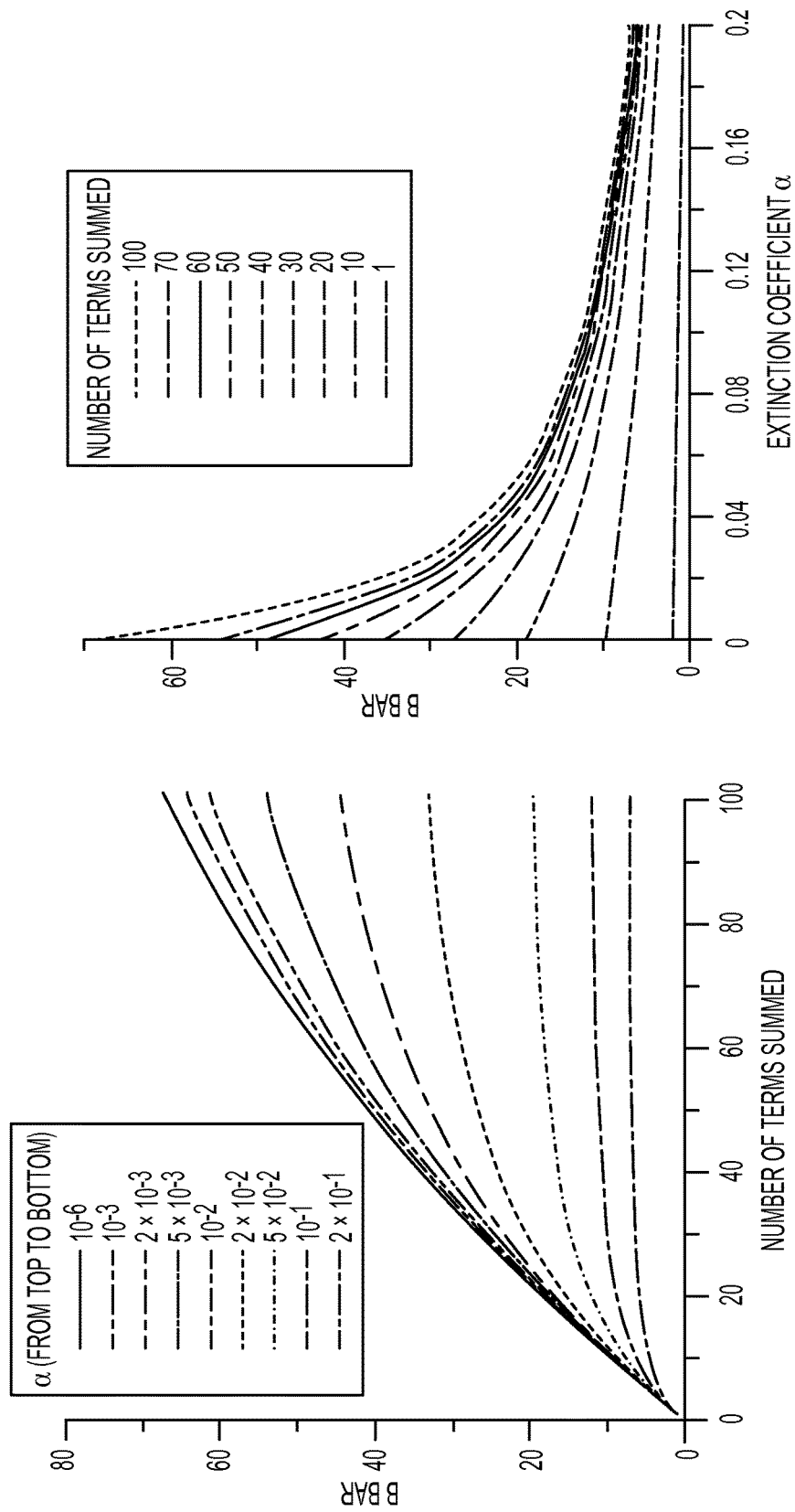

CAVITY ENHANCEMENT METHODS, SYSTEMS AND DEVICES, AND METHODS OF MEASURING SAME

STATEMENT REGARDING FEDERALLY SPONSORED RESEARCH OR DEVELOPMENT

The invention that is the subject of this application was made with U.S. government support under NSF EAGER grant CHE-1246368 awarded by the National Science Foundation. The U.S. government may have certain rights in this invention.

FIELD OF THE INVENTION

This invention relates generally to methods, devices and systems for increasing light throughput in cavity enhanced spectrometry, and a model for cavity enhanced absorption measurements. More specifically, cavity methods, devices and systems are provided to increase light throughput in the cavity without significant loss of cavity enhancement resulting in improvements of detection limits.

BACKGROUND OF THE INVENTION

Absorption spectrometry is arguably the most commonly used quantitation technique used for analysis. To increase detection sensitivity, one chooses the optimum chemistry and the measurement wavelength (absorptivity c at maximum). Absorbance also increases with the pathlength. In the gas phase, single long paths as in differential optical absorption spectroscopy or one attained through multi-reflection cells can be used. Simply increasing the absolute value of the absorbance is not tantamount to improving the limit of detection (LOD), however. In the liquid phase, due to increased beam divergence, light is rapidly lost to the wall and the relative noise increases concomitantly as the detector becomes light starved. Thin walled straight glass tubes or those filled with high refractive index (RI) organic solvents help guide light via total internal reflections at the glass-air and solvent-glass interfaces, respectively; neither system is particularly useful: in one case deposition of any particles on the glass outer surface causes loss of light, in the other case, water is the solvent of interest in majority of applications. A gas shell can be formed around a liquid in a hydrophobic porous membrane tube but a gas bubble is too readily formed. Aqueous solutions containing a lot of solute or ethanol can have an RI greater than that of FEP Teflon® 1.34 and thus a FEP tube filled with such a solution also behaves as a liquid core waveguide (LCW). LCWs with a purely aqueous solution as the core have become practical only after the introduction of Teflon AF (RI 1.29-1.31, compared to 1.33 for water).

In all the above arrangements, the incident light assumedly traces a single path; these are both single path and single-pass cells, i.e., the light does not trace the same path twice. Such cells have a single effective overall pathlength for the purposes of Lambert-Beer's law regardless of the cell contents. If a particular chemistry—wavelength combination leads to a certain dynamic range, changing the pathlength can merely change the location of the usable range in the concentration domain.

In contrast, a multipath arrangement behaves differently. If the shortest path that the light can travel to reach the detector is b, the effective pathlength (henceforth designated $\bar{b}$) is absorbance dependent. It can be perceived that at high absorbances, longer paths contributes little to the transmitted light and $$\lim_{A=\infty} \bar{b} = b.$$

the value of $\bar{b}$ at the lower absorbance limit is of greater interest as it is often the determinant of the concentration limit of detection (LOD). For a multiplicity of pathlengths $b_i$, each having $f_i$ fraction of the total light ($\Sigma f_i = 1$), it has been shown that $\bar{b}$ at the lower absorbance limit is simply the weighted sum $\bar{b} = \Sigma f_i b_i$. For an evenly illuminated wedge shaped cell, for example, at the lower absorbance limit $\bar{b}$ can be half the base width of the cell.

The combination of cells with different pathlengths, as in a wedge-shaped cell, is not practical; moreover, $$\lim_{A=0} \bar{b}$$

can still be less than the longest physical pathlength. Putting partially reflective mirrors on both the entrance and exit windows of any conventional cell can serve the same purpose. Such a system, hereinafter called a single-path multipass cell (multiple reflections on the same path as the beam traverses back and forth, each time losing light both due to absorption by the medium and transmission through the partially transmissive mirrors), is provided in order to increase the pathlength, especially at the low absorbance end.

It can be shown that the gain in pathlength at the low absorbance limit is equal to $$\frac{1+R^2}{1-R^2},$$

where R is the reflectivity of the mirror (R being 1 for a perfectly reflective mirror and 0 for a perfectly transparent object). It can be further shown that for values of R approaching 1

$$\frac{1+R^2}{1-R^2}$$

is well approximated by $$\frac{1}{1-R}.$$

Thus for example, a cell with a physical pathlength of 1 cm, bounded by mirrors of 99% reflectivity (R=0.99) will have an effective path length of $$\bar{b} = \frac{1}{1-R} = 100 \text{ cm.}$$

While an increase in the mirror reflectivity R increases the pathlength and a proportionate amplification of absorbance, increases in R also results in lower light throughput and increases the relative noise of the detector. With R=0.99 mirrors for example, with 10,000 photons incident on the entrance mirror, only 100 photons will make into the cell and if there is no attenuation by the solution in the cell, of 100 photons making it to the exit mirror only 1 will exit to reach the detector. What is needed then is a means for increasing light throughput without significant loss of cavity enhancement and reducing the need for increased source brightness for sufficient light to reach the detector.

SUMMARY

Even with coherent light sources, there can be finite beam divergence. Presented herein are methods, devices and systems for increasing light throughput in cavity enhanced spectrometry in the presence of beam divergence, and a model for cavity enhanced absorption measurements.

In one aspect, a measurement cell comprises a partially reflective entrance mirror and a partially reflective exit mirror defining a cavity therebetween. In another aspect, the entrance mirror can be placed on and/or form at least a portion of a first side of the cell, and the exit mirror can be placed on and/or form at least a portion of a second side of the cell.

An input aperture can be defined in at least a portion of the entrance mirror. In one aspect, while the aperture can be small in an absolute scale, the aperture can be sized and shaped such that the source light can be efficiently and effectively entered into the cell through the aperture. At least a portion of the light entering the cell through the aperture can travel across the cavity and reflect off the exit mirror and back towards the entrance mirror. A portion of this reflected light can be lost from the cell through the aperture defined in the entrance mirror, the extent of the loss depending on the beam divergence. For a divergent beam, when the aperture is made small and the light is focused such that the beam waist enters the aperture (or the divergent source is situated at the aperture), this loss can be small compared to the total beam area. By introducing light into the cell through the aperture defined in the entrance mirror, the overall light throughput in the cell can be increased. As an approximate guide line, with R=0.99 mirrors, if the light enters through the aperture rather than through a mirror, 100 times as much light can enter the cell. The relative noise decreases with the square root of the light intensity; as such, a 10-fold decrease in the noise can be observed.

In use, light emitted from a light source can enter the cell through the input aperture and can be detected by a detector configured to convert light detected into an electrical signal for further analysis by a computer or other processor. The input aperture, in one aspect, can improve light throughput in the cell without significant departure from the theoretically predicted amplification of absorbance. Further, the input aperture can improve light throughput in the cell such that detection limits of the detector are improved, even when used with mirrors of modest reflectivity and inexpensive detectors.

Related methods of operation are also provided. Other apparatuses, methods, systems, features, and advantages of the cavity enhancement system and the method of its use will be or become apparent to one with skill in the art upon examination of the following figures and detailed description. It is intended that all such additional apparatuses, methods, systems, features, and advantages be included within this description, be within the scope of the cavity enhancement system and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 3A is a graph illustrating the effective pathlengths computed for the cell arrangement in FIG. 3B. In this off axis-arrangement, both entrance and exit apertures are present to increase light throughput. The entrance and exit sides (in this aspect, the enclosure) act as reflective mirrors. L is the vertical distance between the entrance and exit point, $\Phi$ is the angle between the vertical distance 'L' and the shortest path length (considered as unity for standard cells), $\theta$ is the angle between the vertical distance 'p' and the shortest path length and 'h' is the distance traveled by the incident light at an angle $\theta$. Note logarithmic axes in the plot. Note also that the shortest source detector distance is $\sqrt{2}$ if this is considered the base path length; the path length amplification factor is ~40% less than the ordinate values shown.

FIG. 3B is schematic view of a single path multipass cell arrangement is which a source is offset from a detector, according to one aspect.

FIG. 4 graphically illustrates the effect of finite number of reflection terms summed in equation 7 for different values of the extinction coefficient $\alpha$ on the effective pathlength $\bar{b}$. If FIG. 4b is plotted with a logarithmic abscissa, qualitatively it can have the same shape as FIGS. 2 and 3.

DESCRIPTION OF THE INVENTION

Figure 1:
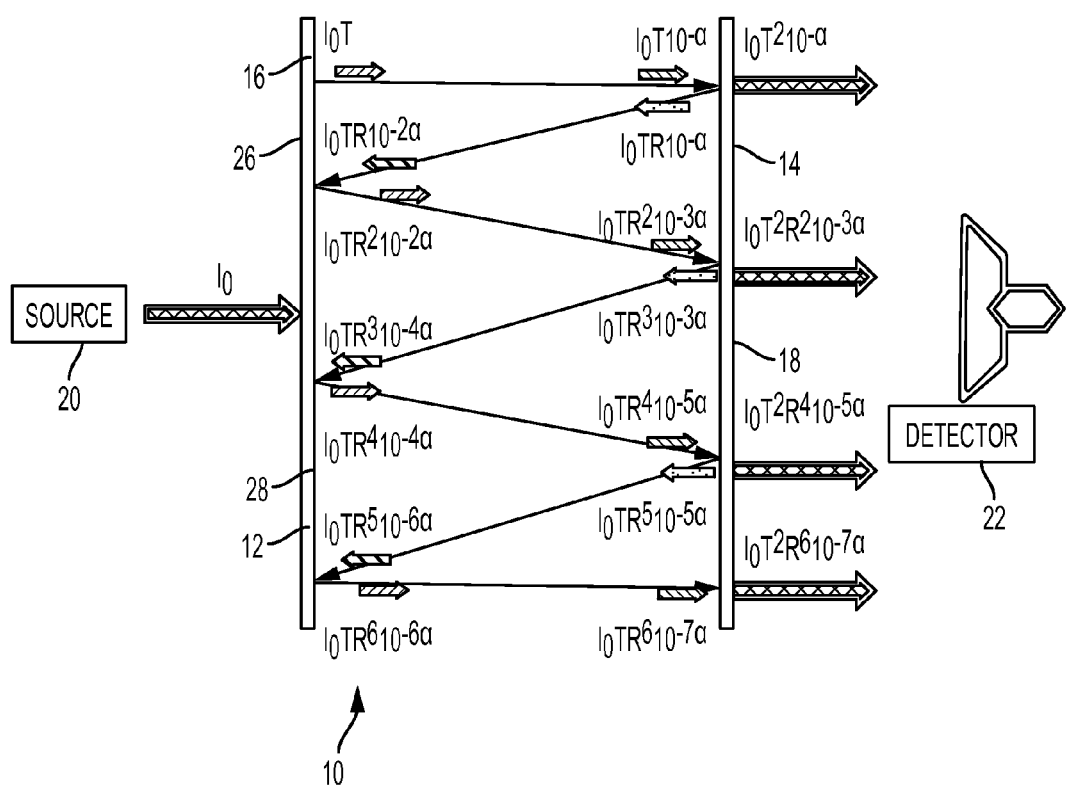
FIG. 1 is a view of a single path multipass cell arrangement, schematically shown, according to one aspect. The individual ray traces are all actually perpendicular to the mirrors and are superimposed on each other. They are shown in this manner to indicate the intensity after each event. Similarly, a single beam emerges to fall on the detector. Mirror reflectance is R, transmittance is T, extinction coefficient of the medium is $\alpha$.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to an "emitter" includes aspects having two or more emitters unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Presented herein, in one aspect, is a generally applicable mathematical foundation for cavity enhanced absorption measurements regardless of the exact values of R (the mirror reflectance), T (the mirror transmittance) and a (the extinction coefficient of the medium). In another aspect, an input aperture for the cavity has been provided which can be of value in situations wherein beam divergence is relatively significant. In this aspect, the input aperture can result in greater light throughput without significant loss of cavity enhancement and thus can reduce the need for increased source brightness for sufficient light to reach a detector.

Optics and the analytical chemistry literature respectively use natural and base-10 logarithmic relationships to describe light extinction. As used herein, the respective extinction coefficients will be denoted as $\alpha'$ and $\alpha(\alpha' = \alpha \ln(10))$, the base-10 version of Lambert's law being $I = I_0 10^{-\alpha b}$, where $I_0$ and $I$ are the total incident and transmitted light intensities, and $\alpha$ is equal to $\in c$, $\in$ being the molar absorptivity of the solute and c its concentration. It is assumed that the base path length b on each side of which a partial mirror can be placed to be unity. Since units are not specified, any conclusion can be equally valid for any other value of b. With $b=1$, $\bar{b}$ is not only the effective pathlength, but it also can be the amplification factor of the physical pathlength, sometimes referred to as the cavity enhancement factor. It is also assumed that $R+T=1$, i.e., mirror absorptance is negligible (note, however, that it can readily be shown that a finite absorptance has no effect on the results, except for a reduction in the overall light throughput).

Although others have considered the theoretical aspects of single path multipass systems, the focus has been on the accurate determination of a, the extinction coefficient of the medium in the cavity. An accurate mathematical description that adequately takes into account finite absorption by the intervening medium has not been given and is provided below.

FIG. 1 depicts a measurement cell 10, according to one aspect. The measurement cell comprises an entrance mirror 12 and an exit mirror 14. In another aspect, at least one of the entrance mirror and the exit mirror can be a partially reflective mirror. In a further aspect, the entrance mirror can be placed on and/or form at least a portion of a first side 16 of the cell 10, and the exit mirror can be placed on and/or form at least a portion of a second side 18 of the cell 10 such that a cavity is defined between the first and second sides. At least a portion of the entrance mirror and/or the exit mirror can be a nonfocusing mirror. In another aspect, at least a portion of the entrance mirror and/or the exit mirror can be substantially planar. The mirror can be formed from a conventional mirror, a silvering solution, aluminized Teflon, aluminized Mylar and the like. In use, light emitted from a light source 20 can enter the cell and can be detected by a detector 22 configured to convert light detected into an electrical signal for further analysis by a computer or other processor.

Following the notations used above, with $I_0$ incident on the entrance mirror, $I_0T$ enters the measurement cell 10. Light reaching the exit mirror 14 is $I_0T10^{-\alpha}$ of which $I_0T^210^{-\alpha}$ is transmitted and $I_0TR10^{-\alpha}$ is reflected. Light is again attenuated as it traverses the cell and reaches the entrance mirror 12 with the intensity $I_0TR10^{-2\alpha}$. $I_0TR^210^{-2\alpha}$ is reflected back, $I_0TR^210^{-3\alpha}$ reaches the exit mirror 14 and $I_0T^2R^210^{-3\alpha}$ is transmitted. The total transmitted light I can be represented by the Infinite geometric series:

$$I = I_0T^210^{-\alpha}\Sigma(1+r+r^2+r^3+r^4+\ldots) \quad (1)$$

where $r = R^210^{-2\alpha}$.

Recognizing that the sum of the geometric series in parentheses is $(1-r)^{-1}$, equation 1 reduces to:

$$I = \frac{I_0T^210^{-\alpha}}{(1-R^210^{-2\alpha})} \quad (2)$$

This leads to the expression of $\bar{b}$:

$$\bar{b} = \frac{1}{\alpha}\log\left(\frac{1-R^210^{-2\alpha}}{10^{-\alpha}(1-R^2)}\right) \quad (3)$$

Note that in deriving equation 3, there was no implicit assumption that mirror absorptance is negligible or that the reflectivity is necessarily very high. Equation 3 can be valid for values of R or values of R+T that are less than and/or significantly less than 1. At the low absorbance limit of equation 3, it can be readily derived that:

$$\lim_{\alpha \to 0} \overline{b} = \frac{1+R^2}{1-R^2} \quad (4)$$

The same system has previously been considered by Dasgupta and Rhee and O'Keefe. However, Dasgupta and Rhee used an interferometric model that is inapplicable here because the bandwidth of the source and the quality of the cavity will not be expected to hold in the present experiments. O'Keefe assumed negligible mirror absorptance and derived (a missing minus sign has been corrected)

$$I = -\frac{I_0 T^2 e^{-\alpha'}}{2 \ln(Re^{-\alpha'})} \quad (5)$$

Equation 5 is normally used to describe cavity absorption behavior at high values of R and low values of α. It is an approximation while the summation of the transmitted light terms (these represent a geometric series) depicted in FIG. 1 provides a globally correct solution in predicting $\overline{b}$ for any value of a or R. O'Keefe did not explicitly calculate the gain in path length but this can be computed from equation 5 to be:

$$\overline{b} = \frac{1}{\alpha'} \ln\left(\frac{\ln(R) - \alpha'}{e^{-\alpha'} \ln(R)}\right) \quad (6)$$

At the low absorbance limit, $$\lim_{\alpha' \to 0} \overline{b} = 1 - \frac{1}{\ln(R)} \quad (7)$$

Figure 2:
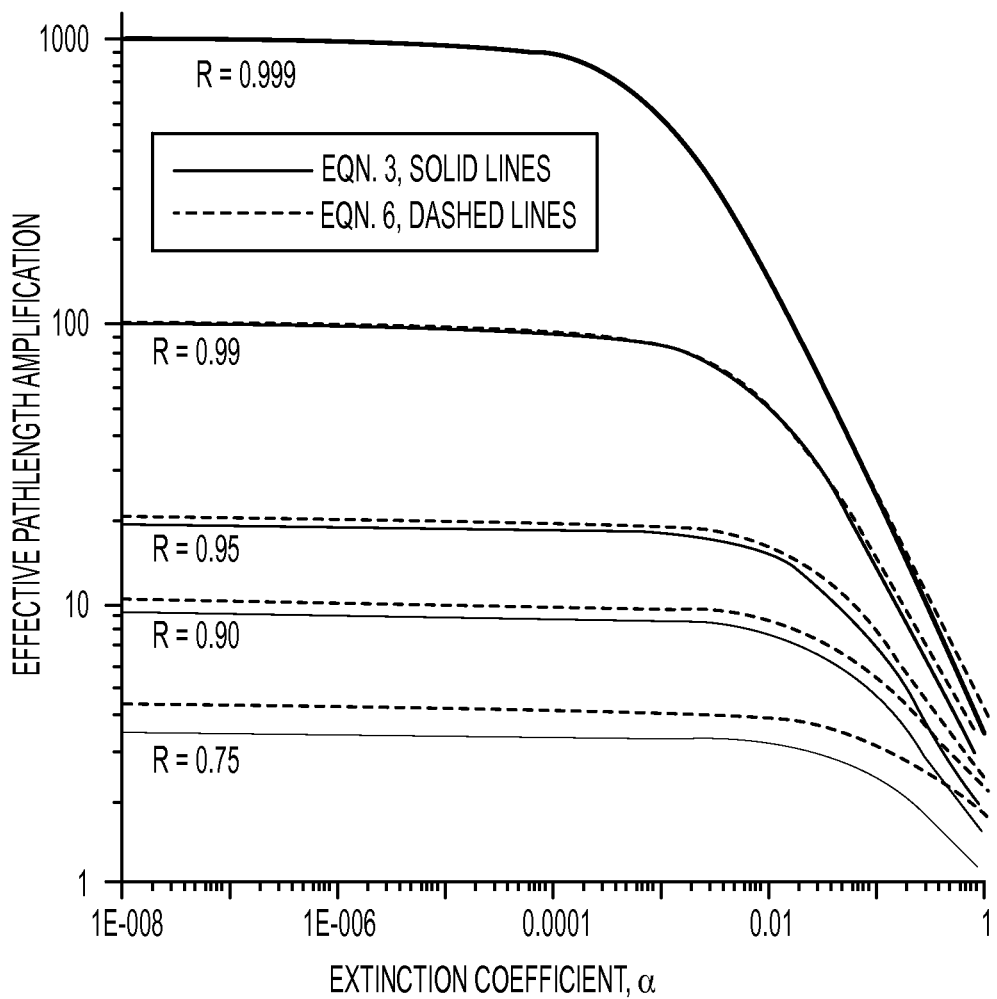
FIG. 2 illustrates graphically the difference between the O'Keefe (equation 5) and the geometric series summation (equation 9) approaches in predicting $\bar{b}$ as a function of $\alpha$ for various values of R.

A comparison of equations 3 and 6 for $\overline{b}$ as a function of a for various values of R appear in FIG. 2. The figure is in logarithmic scale to cover a large span; unfortunately, such scaling also minimizes the visual difference. Nevertheless, it is apparent that the expectations from both equations are nearly the same at high values of R and low values of α and there is significant difference when either R is low or α is high. It can also be noted that for either equation 3 or 6, at high values of R, the limiting value of $\overline{b}$ is approximately given by:

$$\lim_{R \to 1, \alpha \to 0} \overline{b} \cong \frac{1}{1-R} \quad (8)$$

In a nominally single-path multipass system of perpendicular beam incidence, there can be finite beam divergence and a finite detector area. As can be appreciated, all of the light coming out on the detector side cannot be captured by the detector. Thus a real situation likely represents a finite number of reflections. This can be simulated by truncating the infinite series expression in equation 1 to any desired number of terms. The results for 1-100 terms summed for a standard 1 cm path cell 10, for absorbance values ranging from $10^{-6}$ to 0.2 is shown in FIGS. 4a and 4b, according to one aspect. In this aspect, the entrance mirror 12 and the exit mirror 14 have a reflectance R=0.99. Note that "number of terms" is not synonymous with number of passes counted. For example, when three terms are counted, the first term results from a single base path traverse, while the second and the third terms result from three and five base-path traverses, respectively.

As may be intuitive (if the series is limited to a single term, that is standard Beer's law behavior; $\overline{b}$ can be >1 only in the presence of subsequent terms), $\overline{b}$ increases with increasing number of terms summed (FIG. 4a), although even after 100 terms $\overline{b}$ does not reach the limit predicted by equation 4 (compare the FIG. 4a vs. the FIG. 2 R=0.99 trace). Given the same number of terms, $\overline{b}$ can also increase with decreasing α (FIG. 4b), much the same as the infinite series sum in FIG. 2, except that the sum obtained here is less than that from equation 3. In the above considerations, it is assumed that the number of terms that count and the extinction coefficient α are independent variables. In reality, when light loss in each pass is significant (e.g., because of beam divergence and/or R is low, the effective number of terms can decrease with increasing α). A typical detector does not cover all the area through which light can exit through the cell. Although in practice light is reflected around infinitely, effectively only a finite number of reflections, the exact number depends on beam divergence, R, α and the fraction of the total light exit area covered by the detector.

In one aspect, light throughput in the measurement cell 10 can be an important consideration. In a preferred situation, the detector can only be limited by shot-noise. For example, if there are temporal source fluctuations, it is assumed that this can be compensated for by referencing. However, if light reaching the detector 22 is not sufficient (whether because R is too high and/or $I_0$ is too low), increasing the absorbance signal will not necessarily result in any improvement in lowering the limits of detection (LOD) which is typically defined on the basis of Signal/Noise (S/N)=3. Further, counterintuitively, putting mirrors of very high R on each side of a cell in a standard spectrophotometer can deteriorate the LOD, not improve it.

The signal S in the present case is defined as the difference in the amount of light reaching the detector 22 in the presence of an absorbing sample (α=α) from that when α=0. Adapting equation 2:

$$S = I_{\alpha=0} - I_{\alpha=\alpha} = \frac{I_0 T^2}{(1-R^2)} - \frac{I_0 T^2 10^{-\alpha}}{(1-R^2 10^{-2\alpha})} \quad (9)$$

Assuming zero absorptance (R+T=1) equation 9 can reduce to $$S = \frac{I_0 (1-R)\alpha'(1+R^2)}{(1+R)(1-R^2(1-2\alpha'))} \quad (10)$$

Only for R approaching unity, at low values of α, equation 10 can further reduce to $$S = \frac{I_0 \alpha'}{2} \quad (11)$$

In a shot noise limited situation, the noise associated with each of the terms in equation 9 is proportional to the square root of each of the terms. As the noise can add in a root mean square fashion the expression of the overall noise N can be written as:

$$N = k\sqrt{\frac{I_0(1-R)^2}{(1-R^2)} - \frac{I_0(1-R)^2 10^{-\alpha}}{(1-R^2 10^{-2\alpha})}} \quad (12)$$

where k is a constant of proportionality. This equation simplifies to:

$$N = k\sqrt{\frac{1 + (1-\alpha')(1-2R^2)}{(1+R)(1-R^2(1-2\alpha'))}} \quad (13)$$

For R approaching unity, at low values of $\alpha$, equation 13 can further reduce to:

$$N = k\sqrt{I_0(1-R)} \quad (14)$$

leading to the following expressions for S/N and LOD:

$$S/N = 0.5 \frac{\alpha'\sqrt{I_0}}{k(1-R)} \quad (15)$$

$$LOD = 1.5 \frac{\alpha'\sqrt{I_0}}{k(1-R)} \quad (16)$$

In one aspect, the above considerations apply for an incident light beam repeatedly traversing the same path. Effects of beam etendue/divergence or the dependence of the exact reflectance of high-R dielectric mirrors on the incidence angle are not accounted for. However, even for a coherent/collimated beam, some beam divergence is likely upon a large number of reflections. Previously, there have been no theoretical considerations of multiple paths originating from reflections within an enclosure.

When a divergent light source 20 is used, in one aspect and with reference to FIG. 1, the light can be introduced into the cell 10 through an aperture 24 defined in a portion of the entrance mirror 12. At least a portion of the light entering the cell through the aperture can reflect off the exit mirror 14 and back towards the entrance mirror. As can be appreciated, a portion of the reflected light can be lost from the cell through the aperture 24 defined in the entrance mirror. This loss, however, can be small compared to the total beam area of a divergent beam. In another aspect, by introducing light into the cell through the aperture defined in the entrance mirror, the overall light throughput in the cell can be increased by the factor $(1-R_{entrance})^{-1}$.

In one aspect, the aperture 24 defined in a portion of the entrance mirror can be substantially circular in cross-sectional shape. In other aspects, the aperture can be substantially oval, substantially elliptical, or any other shape. The aperture 24 can have a substantially constant diameter, according to one aspect. Alternatively, the diameter of the aperture can increase or decrease as the aperture extends from an outer surface 26 of the entrance mirror to an inner surface 28 of the entrance mirror. In another aspect, the aperture 24 can have a diameter or other dimension (such as height and/or width) of less than about 0.1 mm, about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm or greater than about 10 mm.

In one aspect, the cell 10 can comprise a cuvette 30, such as an externally silvered cuvette as depicted in FIG. 3B and the like. In this aspect, each wall of the cuvette can behave as a mirror. A divergent light source 20, such as, for example and without limitation, a light emitting diode (LED) can be used to input light into the cell through the aperture 24 defined in a portion of the entrance mirror 12 of the first side 16 of the cell. In another aspect, the detector 22 can be positioned on the opposed second side 18 of the cell located at a different horizontal plane relative to the source. That is, the location of the detector can be positioned higher or lower relative to the aperture 24 defined in the entrance mirror. In a further aspect, a longitudinal axis $L_D$ of the detector can be offset a predetermined amount from a longitudinal axis Ls of the source and/or a longitudinal axis $L_I$ of the input aperture.

The detector 22 can be positioned behind the exit mirror 14 to detect light transmitted through the exit mirror. Optionally, an exit bore 32 can be defined in a portion of the exit mirror and/or the second side 18 of the cell and the detector can be positioned behind or otherwise adjacent the exit bore. In one aspect, as long as the detector size is small relative to the beam dimensions from the source, the theoretical considerations can differ little other than an increase in the light throughput by the factor $(1-R_{exit})^{-1}$.

Inside the measurement cell 10, in this aspect, a direct ray of light traveling from the source 20 to the detector 22 can be at an angle $\phi$ relative to the longitudinal axis $L_D$ of the detector and the longitudinal axis Ls of the source and/or the longitudinal axis $L_I$ of the input aperture. For convenience, it is assumed that $\phi$ is $\pi/4$ rad, such that a vertical distance between the source and the detector is the same as the horizontal base path b from the first side 16 of the cell to the opposed second side 18 (b is again assumed to be unity). In another aspect, light can also travel by reflection being incident at some other angle $\theta(0<\theta<\phi)$ and in doing so, the ray of light traverses a distance h, covering a vertical distance of p (equal to tan $\theta$), as indicated. To reach the detector 22 with a vertical rise of unity, these steps should occur n times where n=1/p. The n steps result in a total beam traverse of 2hn; in the process, 2n−1 reflections take place. Note also that hn is equal to 1/sin $\theta$. If $I_{0,\theta}$ is the initial intensity of the beam traveling with the angle $\theta$, the transmitted light intensity $I_\theta$ can be given by:

$$I_\theta = I_{0,\theta} R^{2n-1} 10^{-2hn\alpha} \quad (17)$$

The total transmitted light intensity I is then obtained by integration over $\theta_{0\to\phi}$:

$$I = \int_0^\phi I_{0,\theta} R^{(\frac{2}{\tan\theta}-1)} 10^{-\frac{2\alpha}{\sin\theta}} \quad (18)$$

For $\phi=\pi/4$ rad (45°), equation 18 can be numerically integrated as a function of $\alpha$, with a resolution of 0.56 mrad (0.1°) for various values of R and the results are shown as dashed line traces in FIG. 3. These calculations assume that the initial intensity is the same at all angles, though this of course is not the case for a real LED. If it is assumed that the angular light intensity distribution of the LED is Gaussian and has a full width half maximum of 0.26 rad (15°), $\bar{b}$ can be much higher because the total light throughput shifts to a higher average traversed pathlength. The overall limiting $\bar{b}$ can be less than what is expected in a single-path multipass paradigm as embodied in equation 3.

Figure 7:
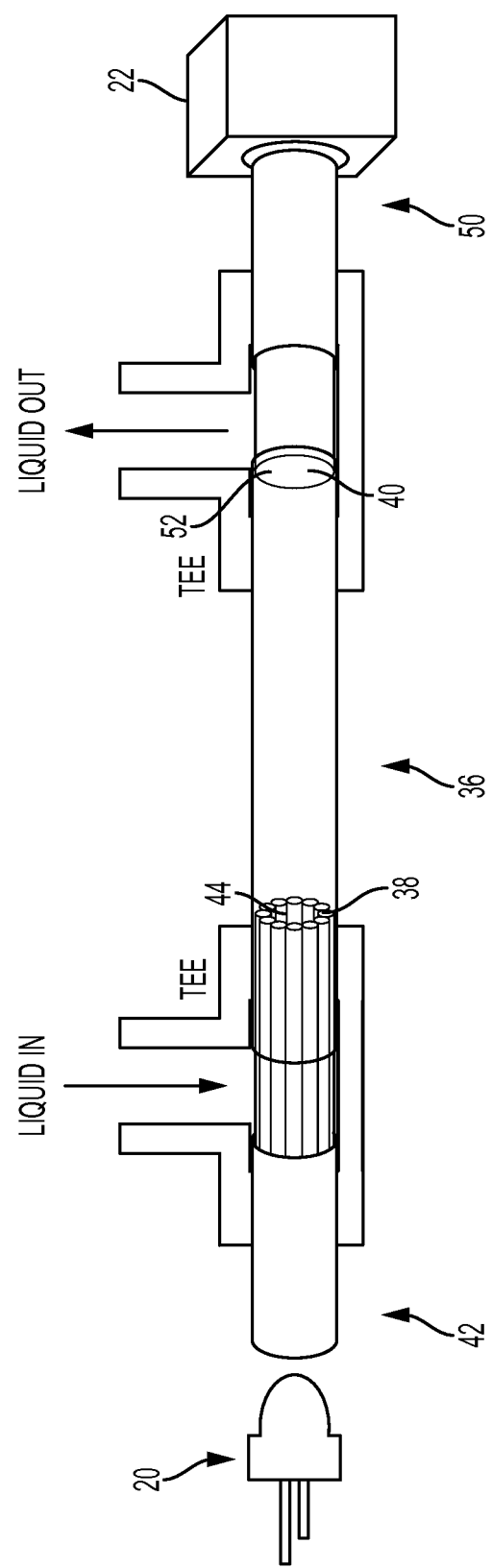
FIG. 7 is a schematic view of a cell arrangement comprising a liquid core waveguide and an optical fiber bundle, according to one aspect.
Figure 8:
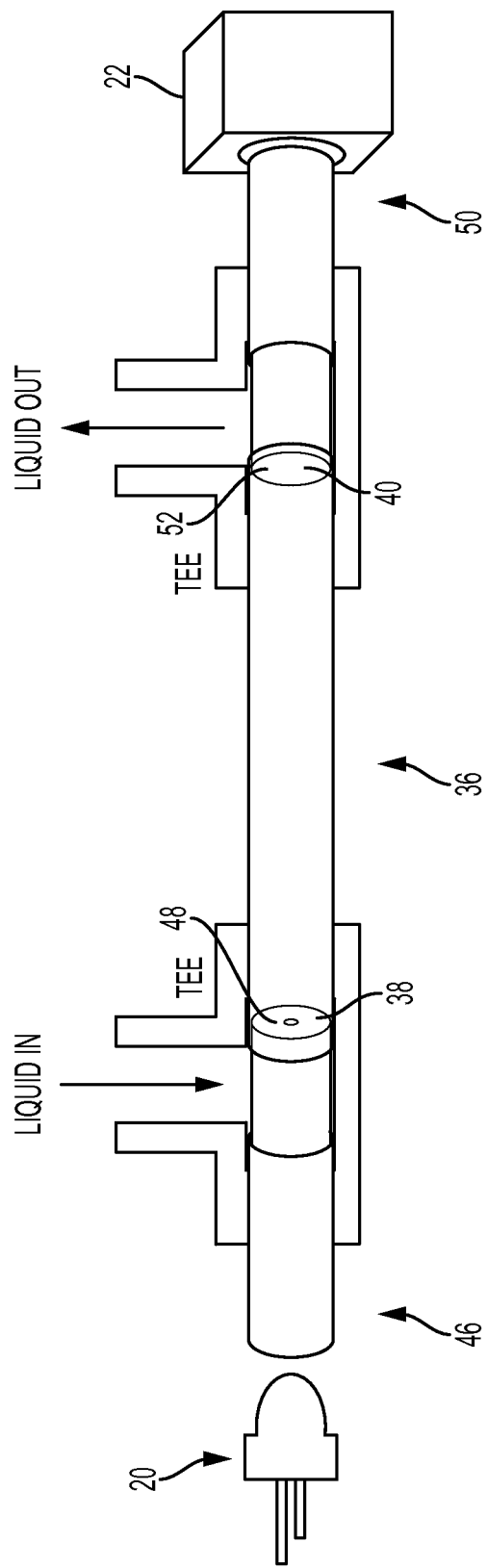
FIG. 8 is a schematic view of a cell arrangement comprising a liquid core waveguide and an optical fiber, according to one aspect.

In one aspect, the measurement cell 10 can comprise the light source 20, the detector 22 and a liquid core waveguide 36 configured to guide light from the light source to the detector as illustrated in FIGS. 7 and 8. In this aspect, the light source can be coupled to an entrance end of the liquid core waveguide, and the detector can be coupled to an exit end of the liquid core waveguide. In use, light emitted from the light source 20 can travel through the liquid core waveguide. In another aspect, the liquid core waveguide can be a tube where light undergoes total internal reflection at the inner or outer surface of the tube. For example, a water filled tube wherein the tube material has a refractive index less than that of water can behave as a liquid core waveguide. In a further aspect, an entrance end wall 38 and an exit end wall 40 of the liquid core waveguide can be at least partially mirrored so that the light can be reflected in the liquid core waveguide 36 as described above. The detector 22 can be positioned adjacent the exit end wall to detect light transmitted through the exit end wall.

With reference to FIG. 7, in one aspect, the entrance end wall 38 can be formed from an optical fiber bundle 42 comprising a plurality of fibers mirrored and for at least one central fiber 44 unmirrored. That is, the central fiber of the optical fiber bundle can be unmirrored to act as the input aperture 24. Referring now to FIG. 8, in another aspect, the entrance end wall 38 can be formed from an optical fiber 46 having a partially mirrored face 48. In this aspect, the input aperture can be an unmirrored portion of the entrance end wall. For example, a central portion of the face of the optical fiber can be unmirrored, and the remaining, surrounding portion of the face 48 of the optical fiber 46 can be mirrored. The exit end wall 40 can be formed from an optical fiber 50 having a mirrored exit face 52. For example and without limitation, the exit end wall can be formed from a mirrored single core optical fiber.

Unlike other cells known and described in the literature, e.g., the Pfund cell, White cell, the Herriott cell where light may undergo multiple reflections but the focused beam (where focus is maintained by the use of concave mirrors) traces a single path, in this measurement cell 10, the deliberately divergent beam and flat surface nonfocusing mirror can result in a highly nonlinear absorbance-concentration behavior. This nonlinearity effectively increases the dynamic range of concentration that can be measured.

Experimental Section

An experiment was conducted with two types of detection arrangements and disposable polystyrene cuvettes in three designs. The detectors 22 ranged from a high end commercial double-beam double monochromator spectrometer capable of reading ±6.000 absorbance (http://www.shimadzu.com/an/spectro/uv/uv3600.html), to an inexpensive fiber optic 12-bit CCD spectrometer (http://oceanoptics.com/products/usb2000.asp, now obsolete). The spectrophotometer measurements were made at the absorption maximum, with a slit width of 2 nm, except as stated. An identically prepared cell 10 filled with water was used as the reference. With the CCD spectrometer, LEDs (center wavelengths of 617 and 522 nm) were used as the light source 20, generally just glued on the cell 10; the drive current was 50 mA. The detector integration time was typically 1.5 seconds. The same experiment was repeated using a 633 nm laser as the source.

The following were the three cell designs: (1) the cell 10 was wrapped with a single layer of reflective aluminized Mylar™ film (0.125 mm thick, sold as disposable emergency thermal blanket, www.sears.com). The aperture 24 was made on the light entrance side 16 of the cell positioned at the incident beam spot center (for the spectrophotometer, a rectangular 1×1.5 mm (w×h) aperture, for the fiber-optic CCD a 0.8 mm diameter cutout). (2) Microscope slides were mirrored using a commercial silvering solution (www.peacocklabs.com), these were affixed on the light entrance and exit sides of the cell. By etching with $HNO_3$, a ~0.5 mm aperture 24 was made on the metaled side at the incident beam center. The glass sides of each mirror faced the cuvettes while the metaled sides were protected with a thin layer of transparent optical grade epoxy. (3) The cell 10 was essentially identical to that in (2) except that the optical fiber of the detector 22 was at a horizontal plane 1.8 cm higher relative to the source aperture 24 (vertically offset, cf. FIG. 3B; this arrangement is hereinafter referred to as off-axis). Also in this off-axis case, light was read through a 0.5 mm bore 32 in the exit-side mirror, unlike setup (2), where light was read through the mirror itself, without a bore.

To make performance comparisons with and without reflective elements, the same type of cells, without any reflective elements, was used. To calculate effective path lengths ($\bar{b}$), the observed absorbance in the reflective cells was divided by the observed absorbance in the standard transparent cells. However, because the absorbance in the standard transparent cells was not directly measurable at very low concentrations, it was obtained by making Beer's law plots for each test dye (Bromocresol Green, Bromthymol Blue, and Erythrosine B (FD&C Red No. 3) in the 0.010-1.000 absorbance range, respectively at 617, 615, and 522 nm. The first two were prepared in 1 mM NaOH; this was also used as the reference solution. Erythrosine was prepared in water. Standard laboratory reagents were used. Diluted standards were typically prepared immediately before use, at the lowest concentrations, often in the measurement cell itself to prevent adsorption losses.

The Y-intercepts in the above Beer's law plots were statistically indistinguishable from zero, the linear relationship was excellent ($r^2 \geq 0.999$), and the molar absorptivities ($\in$) calculated from the slope were in excellent agreement with literature values. The absorbance in the conventional cell expected for the dye at the low concentrations was then computed from $\in$.

Reflectivities were measured typically at three wavelengths, using 633 nm (He—Ne), 532 nm (frequency doubled Nd-YAG) and 405 nm (InGaN) lasers and a laser power meter (www.sperdirect.com).

Cell types 1 and 2 were examined with both the spectrophotometer and the CCD spectrometer, cell type 3 was examined only with the latter.

Results

Concentration—Apparent Absorbance Relationships.

Figure 5B:
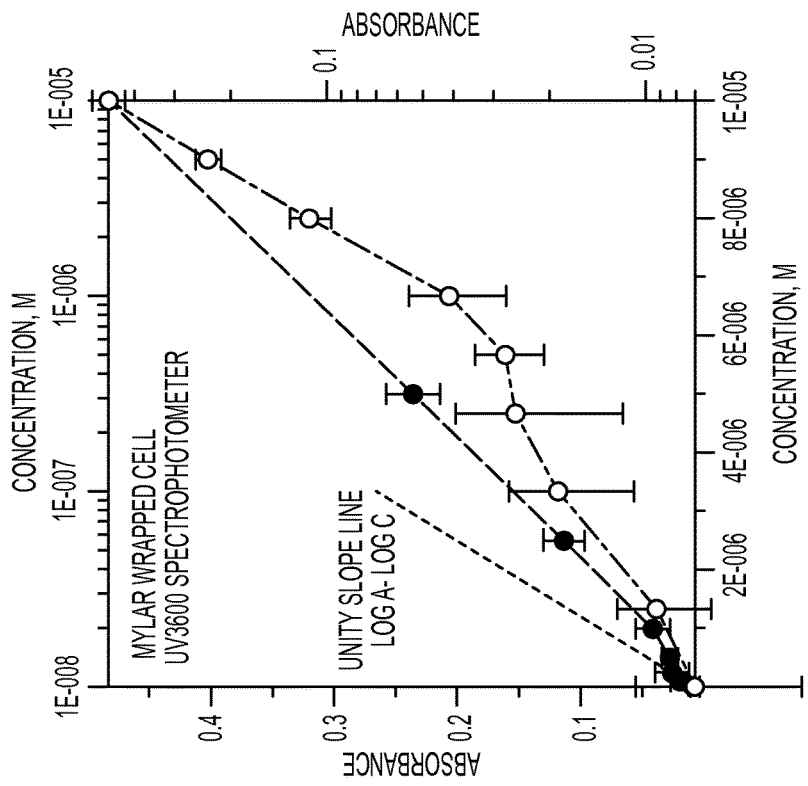
FIGS. 5A and 5B are graphs illustrating Beer's law behavior of Bromocresol Green at pH 12 in conventional linear as well as logarithmic axes.
Figure 5A:
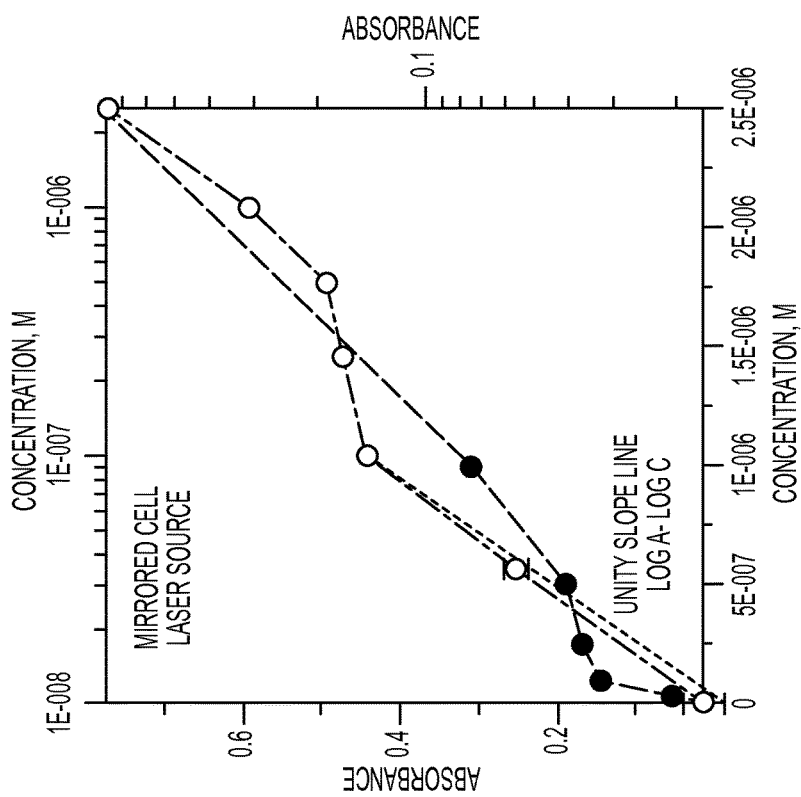
Figures 6A, 6B:
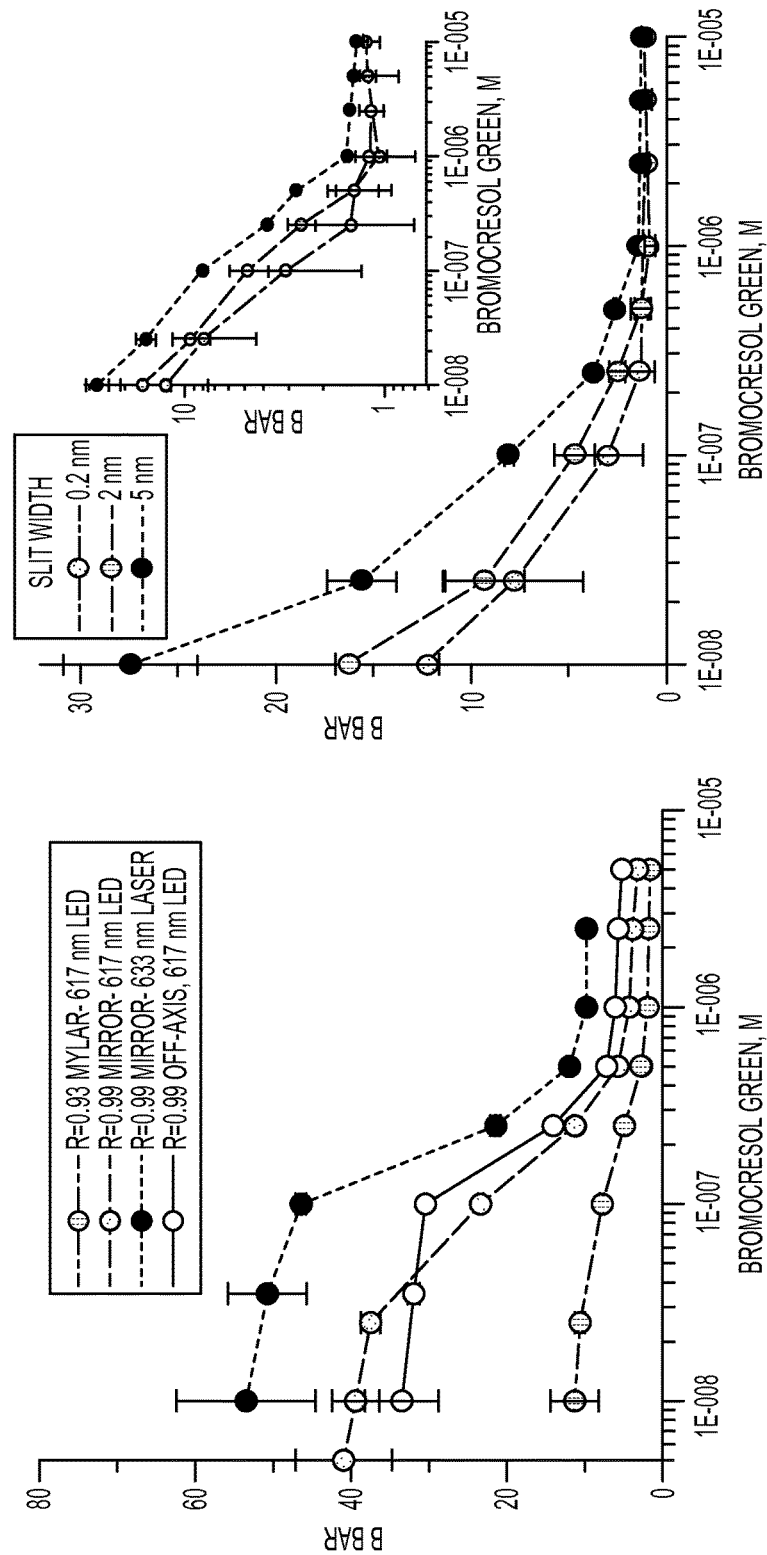
FIGS. 6A and 6B are graphs illustrating the experimental values of $\bar{b}$ as a function of Bromocresol Green concentrations with different cell types and (a) CCD spectrometer detector, (b) UV 3600 Spectrophotometer detector, R=0.99 mirrors. The inset shows the same data but with the ordinate on a logarithmic scale.

FIG. 5 shows Beer's law behavior of bromocresol green at pH 12 in conventional linear as well as logarithmic axes. The beginning and ending values of both axes were the same such that the starting and the ending points in both the linear and logarithmic plots are coincident. Two representative cases are shown: (a) in a silver-mirrored cell (type 2) with a 633 nm laser and a CCD array detector; and (b) a reflective mylar-wrapped cell with the UV 3600 spectrophotometer as the source (617 nm, 2 nm slit width) and detector. In FIG. 5A, referring to the linear axes there are three distinct regions: (i) a very steep A vs C linear relationship at the low concentration end, (ii) a less steep linear portion at the higher concentration end, and (iii) a transition region of low slope in-between. The ratio of the two slopes in (i) and (ii) is the plateau value of the pathlength amplification factor in FIG. 2 and the plateau is attained in region (i). The same three regions are also observed in the log-log plot; the noteworthy item is that log A-log C slope is very close to unity in both regions (i) and (ii). We refer to this as type A behavior, in which plateau value is reached.

FIG. 5B shows the other type of behavior: while this also exhibits three regions and the log A-log C relationship has a unit slope at the higher concentration end, the log A-log C slope is less than unity at the lower concentration end. In this type of behavior (hereinafter called type B) a plateau of pathlength amplification factor is not observed; this will become more apparent in the next section. The data in FIG. 5B also show a greater standard deviation relative to that in FIG. 5A because of poor light throughput resulting from a broadband source and a narrow slit width. An increased slit width increases light throughput and reduces the standard deviation of the measurements (it also increases the effective pathlength amplification factor); all LOD data for the spectrophotometric measurements are therefore reported for measurements made with a 20 nm slit width.

The Limiting Value of $\bar{b}$.

Two basic types of concentration vs. $\bar{b}$ behavior were observed. In the first type of behavior (case A—this includes all experiments with the CCD spectrometer and laser or narrow angle LED sources), the results were in accordance with the theoretical expectations depicted in FIGS. 2, 3, and 4b—namely, a limiting plateau value of $\bar{b}$ was attained or approached (FIG. 5a). The observed $$\lim_{\alpha \to 0} \bar{b}$$

value was also quantitatively close to the theoretically expected $\bar{b}$ values. For example, in the laser source experiment (green trace, FIG. 5a) the $$\lim_{\alpha \to 0} \bar{b}$$

was ~55, which would be expected for mirrors with R=0.982, the measured R was 0.99±0.01. The identical experiment, except with a more divergent LED source, can be expected to have a lower limiting $\bar{b}$ because of earlier series truncation, $$\lim_{\alpha \to 0} \bar{b}$$

in this case (red trace, FIG. 5a) was ~40. For a 15° FWHM LED, for R=0.99 case A, a $$\lim_{\alpha \to 0} \bar{b}$$

of 30 was calculated (FIG. 2) and the experimental $$\lim_{\alpha \to 0} \bar{b}$$

value was ~35. For R=0.93, $$\lim_{\alpha \to 0} \bar{b}$$

was expected to be 13.8 (equation 4) and the observed value at the lowest measured concentration was 11.3±3.1.

In case B (the second type of behavior), there was no indication that a limiting plateau value of $\bar{b}$ was being approached. Rather, $\bar{b}$ increased exponentially with decreasing log (concentration), within the lower limits of the analyte concentrations that could be reliably measured, as shown in FIG. 5b. All spectrophotometer experiments exhibited this type of behavior. Case B behavior can be associated with beam divergence and can also be observed in the CCD spectrometer experiments if wide angle emitters are used, instead of a narrow beam (15° FWHM) LED. Increasing spectrophotometer slit width increases beam divergence and as FIG. 5b shows, the observed effect is more pronounced. Although a quantitative relationship has not been formulated herein, this behavior can be expected if the number of terms that matter in a truncated series increases with decreasing α. For similar reasons (because extinction is more rapid) this effect is also expected with decreasing mirror reflectivity. The observed absorbance (directly proportional to $\bar{b}$)—concentration relationship can be different in case A than in case B. In case A, if $\bar{b}$ has reached a constant limiting value, then absorbance is directly proportional to concentration and this value of $\bar{b}$ is synonymous with the term "Cavity Enhancement Factor" and Lambert-Beer's law can be followed in the $\bar{b}$ plateau region. On the other hand, when $\bar{b}$ increases exponentially with decreasing log C, Lambert-Beer's law can be not followed. log A (or log $\bar{b}$) is linearly related to log C in this regime, as shown in the inset of FIG. 5b. Of course, in case A, when A is linearly related to C with a near-zero intercept, log A can also necessarily be linearly related to log C. In contrast, in case B, A is not necessarily linearly related to C.

Increasing the absorbance has no practical value unless there is actual gain in the limit of detection (LOD). Tables I and II list the observed experimental data for the CCD spectrometer and the spectrophotometer, respectively that demonstrate that real improvements in LODs are achieved.

The LODs were calculated by two different methods. One method assumed a linear relationship between A and C and the other method assumed a linear relationship between log A and log C. The absorbance of the blank was measured five times and the LOD was taken to be the C value corresponding to three times the standard deviation of the blank on the A vs C or log A vs log C plot, respectively. The two calculated LOD values differed significantly only in case B, when A was not linearly related to C. These cases are indicated in the tables with asterisks and in these cases the logarithmic relationship based LOD can be more appropriate. For comparison, measurements were also made in a conventional (no mirrors) cell. The linear relationship between A and C was confirmed in the absence of mirrors and the LOD was computed from slope of the terminal two points above the LOD and three times the uncertainty of the blank as indicated above. In all cases the LOD improved in the cavity enhanced measurements, in some cases by more than an order of magnitude.

TABLE I

Summary of Results, CCD Spectrometer Detector

| Cell type | Analyte | Reflectivity | Lowest tested concn., nM[a] | Effective pathlength at lowest concn., $\bar{b}$ cm | $LOD_1$, nM[b] | $LOD_2$, nM[c] |
|---|---|---|---|---|---|---|
| Conventional, no mirror | Bromocresol green, $\epsilon = 39100\ M^{-1}\ cm^{-1}$ | NA | | 1 | 36 | |
| Type 1: Reflective Mylar, entrance aperture, 617 nm LED | Bromocresol green | 0.93 @ 633 nm | 10 | 11 ± 0.5 | 8 | 8 |
| Type 2: Glass mirror, entrance aperture, 617 nm LED | Bromocresol green | 0.99 @ 633 nm | 10 | 41 ± 3.2 | 4 | 4 |
| Type 2: 633 nm laser source | Bromocresol green | 0.99 @ 633 nm | 10 | 55 ± 16 | 3 | 3 |
| Type 3, Off-axis 617 nm LED | Bromocresol green | 0.99 @ 633 nm | 10 | 33 ± 4.7 | 12 | 9 |
| Conventional, no mirror | Erythrosine $\epsilon = 87,500$ | NA | 25 | 1 | 46 | |
| Type 1: Reflective Mylar, entrance aperture, 522 nm LED* | Erythrosine | 0.89 @ 532 nm | 25 | 8.2 ± 0.8 | 5 | 4 |
| Type 2: Glass mirror, entrance aperture, 522 nm LED* | Erythrosine | 0.91 @ 532 nm | 25 | 8.8 ± 0.3 | 4 | 0.4 |

[a]lowest concentration measured; not considered if below the LOD
[b]Based on the terminal slope of the Absorbance vs concentration curve
[c]Based on the terminal slope of the log (Absorbance) vs log (concentration) curve
*at low concentrations, log A varies linearly with log C.

TABLE II

Summary of Results, UV Spectrophotometer Detector*

| Cell type | Analyte | Reflectivity | Lowest tested Concn, nM[a] | Effective pathlength at lowest concn, $\bar{b}$ | $LOD_1$, nM[b] | $LOD_2$, nM[c] |
|---|---|---|---|---|---|---|
| Conventional, no mirror | Bromocresol green @ 617 nm | | | | 47 | |
| Type 1: Reflective Mylar, Entrance Aperture | Bromocresol Green @ 617 nm | 0.93 @ 633 nm | 10 | 16 ± 4.6 | 33 | 5 |
| Type 2: Glass Mirror, Entrance Aperture | Bromocresol green @ 617 nm | 0.99 @ 633 nm | 25 | 95 ± 23 | 6 | 0.4 |
| Conventional, no mirror | Erythrosine @ 522 nm | | | | 13 | |
| Type 1: Reflective Mylar, Entrance Aperture | Erythrosine @ 522 nm | 0.89 @ 532 nm | 12.5 | 26 ± 4.3 | 8 | 7.3 |
| Type 2: Glass Mirror, Entrance Aperture | Erythrosine @ 522 nm | 0.91 @ 532 nm | 12.5 | 48 ± 12 | 10 | 7.2 |

*at low concentrations, log A varies linearly with log C.
[a]lowest concentration measured; not considered if below the LOD
[b]Based on the terminal slope of the Absorbance vs concentration curve
[c]Based on the terminal slope of the log (Absorbance) vs log (concentration) curve In summary, in one aspect, a generally applicable (regardless of the exact values of R, T or $\alpha$), mathematical foundation for cavity enhanced absorption measurements has been provided. In another aspect, an input aperture 24 for the cell 10 has been provided which can be of value in a situation where beam divergence is present. This can result in greater light throughput without significant loss of cavity enhancement and thus reduces the need for increased source brightness for sufficient light to reach the detector for shot noise limited operation. This can provide an attractive means to make sensitive absorbance measurements with good light throughput in systems where the physical pathlength is limited, e.g., in capillary systems. It has also been shown that similar nonlinear absorbance amplification can result from the multipath effect in a reflecting cavity that contains an entrance and additionally an optional exit bore that do not necessarily directly face each other.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A cell for absorbance measurements of a medium positioned in a cavity of the cell comprising;
    an entrance mirror forming at least a portion of a first wall of the cell, wherein an input aperture is defined in a portion of the entrance mirror, wherein the input aperture is substantially circular in cross-sectional shape and wherein a diameter of the input aperture decreases as the aperture extends from an outer surface of the entrance mirror to an inner surface of the entrance mirror;
    an exit mirror forming at least a portion of a second wall of the cell that is opposed to the first wall;
    a light source configured to input a beam of light into the cavity of the cell through the input aperture; and
    a detector positioned outside of the cell adjacent to the exit mirror configured to convert light detected exiting the cell through the exit mirror into an electrical signal for further analysis by a processor.

2. The cell of claim 1, wherein the beam of light is a divergent beam.

3. The cell of claim 2, wherein at least a portion of the light entering the cell through the input aperture travel across the cavity and reflects off the exit mirror and back towards the entrance mirror.

4. The cell of claim 3, wherein a portion of the light reflected back towards the entrance mirror is lost from the cell through the input aperture.

5. The cell of claim 4, wherein the input aperture is sized so that the lost light is small relative to a total area of the beam of light.

6. The cell of claim 1, wherein the medium is in a gaseous phase.

7. The cell of claim 1, wherein the detector is positioned outside of the cell adjacent to the exit mirror at a different horizontal plane relative to the input aperture.

8. The cell of claim 7, wherein a longitudinal axis of the detector is offset from a longitudinal axis of the input aperture a predetermined amount.

9. The cell of claim 1, wherein an exit bore is defined in a portion of the exit mirror, and wherein the detector is positioned adjacent the exit bore.

10. The cell of claim 1, wherein the entrance mirror is a nonfocusing mirror.

11. The cell of claim 10, wherein the exit mirror is a nonfocusing mirror.

12. The cell of claim 1, wherein the entrance mirror is substantially planar.

13. The cell of claim 12, wherein the exit mirror is substantially planar.

14. The cell of claim 1, wherein the cell further comprises a liquid core waveguide, wherein the light source is coupled to an entrance end of the liquid core waveguide, and the detector is coupled to an exit end of the liquid core waveguide.

15. The cell of claim 14, wherein the entrance mirror comprises an optical fiber having a mirrored entrance face, and wherein the exit mirror comprises an optical fiber having a mirrored exit face.

16. The cell of claim 15, wherein the input aperture is defined in the mirrored entrance face.

17. A method of improving light throughput in absorption spectrometry comprising:
    providing a cell for absorbance measurements of a medium positioned in a cavity of the cell comprising;
        an entrance mirror forming at least a portion of a first wall of the cell;
        an exit mirror forming at least a portion of a second wall of the cell that is opposed to the first wall;
        a light source; and
        a detector positioned outside of the cell adjacent to the exit mirror configured to convert light detected exiting the cell through the exit mirror into an electrical signal for further analysis by a processor;
    defining an input aperture in a portion of the entrance mirror, wherein the input aperture is substantially circular in cross-sectional shape and wherein a diameter of the input aperture decreases as the aperture extends from an outer surface of the entrance mirror to an inner surface of the entrance mirror; and
    inputting a divergent beam of light into the cavity of the cell through the input aperture.

18. A method of increasing the detection sensitivity of absorption spectroscopy comprising:
    providing a cell for absorbance measurements of a medium positioned in a cavity of the cell comprising;
        an entrance mirror forming at least a portion of a first wall of the cell;
        an exit mirror forming at least a portion of a second wall of the cell that is opposed to the first wall;
        a light source; and
        a detector positioned outside of the cell adjacent to the exit mirror configured to convert light detected exiting the cell through the exit mirror into an electrical signal for further analysis by a processor;
    defining an input aperture in a portion of the entrance mirror, wherein the input aperture is substantially circular in cross-sectional shape and wherein a diameter of the input aperture decreases as the aperture extends from an outer surface of the entrance mirror to an inner surface of the entrance mirror; and
    inputting a divergent beam of light from the light source into the cavity of the cell through the input aperture.

* * * * *